(12) United States Patent
Khanna et al.

(10) Patent No.: US 7,482,463 B2
(45) Date of Patent: Jan. 27, 2009

(54) AMORPHOUS FORM OF ESOMEPRAZOLE SALTS

(75) Inventors: Mahavir Singh Khanna, Delhi (IN); Bakthavathsalan Vijayaraghavan, Haryana (IN); Mohan Prasad, Haryana (IN); Yatendra Kumar, Haryana (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 0 days.

(21) Appl. No.: 11/946,193

(22) Filed: Nov. 28, 2007

(65) Prior Publication Data
US 2008/0119654 A1    May 22, 2008

Related U.S. Application Data

(62) Division of application No. 10/690,897, filed on Oct. 22, 2003.

(30) Foreign Application Priority Data
Oct. 22, 2002   (IN) .................. 1057/DEL/2002

(51) Int. Cl.
C07D 401/12    (2006.01)
(52) U.S. Cl. .................................. 546/273.7
(58) Field of Classification Search ............... 546/273.7
See application file for complete search history.

(56) References Cited

U.S. PATENT DOCUMENTS

| | | | |
|---|---|---|---|
| 4,255,431 A | 3/1981 | Junggren et al. | 424/263 |
| 4,738,974 A | 4/1988 | Brändström | 514/338 |
| 5,714,504 A | 2/1998 | Lindberg et al. | 514/338 |
| 5,714,505 A | 2/1998 | Hasselkus | 514/338 |
| 6,124,464 A | 9/2000 | Högberg et al. | 546/273.7 |
| 6,162,816 A | 12/2000 | Bohlin et al. | 514/338 |
| 6,207,188 B1 | 3/2001 | Gustavsson et al. | 424/464 |
| 6,369,085 B1 | 4/2002 | Cotton et al. | 514/338 |
| 6,713,495 B1 | 3/2004 | Sherman | 514/338 |
| 2003/0181487 A1 | 9/2003 | Kamiyama et al. | 514/338 |
| 2003/0212274 A1 | 11/2003 | Vijayaraghavan et al. | 546/2 |
| 2004/0209118 A1 | 10/2004 | Seo et al. | 428/690 |

FOREIGN PATENT DOCUMENTS

| | | |
|---|---|---|
| EP | 1 375 497 | 1/2004 |
| WO | WO 94/27988 | 12/1994 |
| WO | WO 96/02535 | 2/1996 |
| WO | WO 98/54171 | 12/1998 |
| WO | WO 01/14367 | 3/2001 |
| WO | WO 01/87831 | 11/2001 |
| WO | WO 2004/002982 | 1/2004 |

OTHER PUBLICATIONS

Nerurkar et al., 2000. Properties of Solids That Affect Transport. In: Transport Processes in Pharmaceutical Systems. USA:Marcel Dekker, Inc., 575-610.
Chopra and Dhall, "Formulation and the Solid State of Drugs", Pharmacos, 25:39-45 (1981).
Caira, 1998. Crystalline Polymorphism of Organic Compounds. In:Weber, ed. Design of Organic Solids (Topics in Current Chemistry vol. 198). Germany:Springer-Verlag Berlin Heidelberg, 163-208.
Threifall, "Analysis of Organic Polymorphs. A Review", Analyst, 120:2435-2460 (1995).
Rouhi, "The Right Stuff. From research and development to the clinic, getting drug crystals right is full of pitfalls", Chemical & Engineering News, 81(8):32-35 (2003).
Muzaffar and Sheikh, "Polymorphism and Drug Availability. A Review", Journal of Pharamcy (Lahore), 1(1):59-66 (1979).
Bernstein, 2002. Polymorphism in Molecular Crystals. New York, USA:Oxford University Press. 117-118 and 272-273.
Xu, "DVS—an easy and primary approach to the determination of the solid state of materials", Journal of Zhejiang University of Technology, 31(4):456-459 (2003)—Article and English Abstract.
Doelker, "Physiochemical behaviors of active substances their consequences for the feasibility and the stability of pharmaceutical forms", S.T.P. Pharma Pratiques, 9(5):399-409 (1999)—English Translation.

Primary Examiner—Patricia L Morris
(74) Attorney, Agent, or Firm—Jayadeep R. Deshmukh, Esq.; George E. Heibel, Esq.

(57) ABSTRACT

The invention relates to an amorphous form of the salts of the (-) enantiomer or (S)-enantiomer of omeprazole, i.e., esomeprazole. The invention also relates to processes for preparing amorphous esomeprazole salts and pharmaceutical compositions that include the amorphous esomeprazole salts.

16 Claims, No Drawings ium, in the prior art. It is known that different morphs of biologically active compounds may have different absorption profile in vivo and consequently different pharmacokinetic profile.

AMORPHOUS FORM OF ESOMEPRAZOLE SALTS

This application is a divisional application of U.S. patent application Ser. No. 10/690,897, filed Oct. 22, 2003.

FIELD OF THE INVENTION

The field of the invention relates to an amorphous form of the salts of the (-) enantiomer or (S)-enantiomer of omeprazole, i.e., esomeprazole. The invention also relates to processes for preparing amorphous esomeprazole salts and pharmaceutical compositions that include the amorphous esomeprazole salts.

BACKGROUND OF THE INVENTION

Chemically, omeprazole is 5-methoxy-2-[[(4-methoxy-3, 5-dimethyl-2-pyridinyl)-methyl]sulfinyl]-1H-benzimidazole. Omeprazole and therapeutically acceptable salts thereof are described in U.S. Pat. No. 4,255,431. Certain specific alkaline salts of omeprazole are disclosed in U.S. Pat. No. 4,738,974. Omeprazole is transformed into an effective inhibitor of gastric acid secretion in mammals, and is therefore useful as an anti-ulcer agent. Omeprazole may be used to prevent and/or treat gastric acid related disorders and gastrointestinal inflammatory diseases in mammals. In man, for example, omeprazole may be used to prevent and/or treat gastritis, gastric ulcer and duodenal ulcer.

Omeprazole is a racemic mixture of its two single enantiomers, the (R)- and (S)-enantiomer of omeprazole. These enantiomers are commonly referred to as (R)-omeprazole and (S)-omeprazole, respectively. The enantiomer, (S)-omeprazole, is commonly referred to as esomeprazole.

WO 94/27988 discloses certain salts of the single enantiomers of omeprazole and their preparation. These compounds are described as having improved pharmacokinetic properties which give an improved therapeutic profile, such as a lower degree of variation between individuals taking the compound.

WO 96/02535 discloses a process for preparing the single enantiomers of omeprazole and salts thereof. WO 98/54171 discloses a process for the preparation of the trihydrate of the magnesium salt of (ES)-omeprazole.

Esomeprazole, like many other similar benzimidazole compounds, is not stable in its free form and is susceptible to degradation in acid and neutral media. It has been found that alkali metal or alkaline earth metal salts of esomeprazole are more stable during storage than the corresponding neutral form.

U.S. Pat. No. 5,714,505 describes alkaline salts of the (-) enantiomer of 5-methoxy-2-[[(4-methoxy-3,5-dimethyl-2-pyridiniyl)methyl]sulfinyl]-1H-benzimidazoles (i.e., esomeprazole) including the magnesium salt, which are used for inhibiting gastric acid secretion. Esomeprazole magnesium is prepared according to Examples 5, 6, and 7 of the '505 patent in optically pure crystalline form by precipitation/crystallization.

U.S. Pat. No. 6,124,464 discloses another process for preparing crystalline esomeprazole magnesium. U.S. Pat. No. 6,369,085 discloses three different types of crystalline esomeprazole magnesium viz. dihydrate form A, dihydrate form B and the trihydrate form. However, the inventors are not aware of any disclosure of an amorphous form of esomeprazole salts, including amorphous esomeprazole magnesium, in the prior art. It is known that different morphs of

SUMMARY OF THE INVENTION

In one general aspect there is provided an amorphous form of a salt of esomeprazole.

Embodiments of the amorphous form of the salt of esomeprazole may include one or more of the following features. For example, the cation may be selected from the group that includes Na, Mg, Li, K, Ca, and N(R)$_4$, where R is hydrogen or an alkyl with 1-4 carbon atoms.

The amorphous form of the salt of esomeprazole may have the X-ray diffraction pattern of a plain halo, which demonstrates the amorphous nature of the product.

In another general aspect there is provided a pharmaceutical composition that includes a therapeutically effective amount of an amorphous form of a salt of esomeprazole; and one or more pharmaceutically acceptable carriers, excipients or diluents.

Embodiments of the pharmaceutical composition may include one or more of the following features. For example, the cation may be selected from the group that includes Na, Mg, Li, K, Ca, and N(R)$_4$, where R is hydrogen or an alkyl with 1-4 carbon atoms.

The amorphous form of the salt of esomeprazole may have the X-ray diffraction pattern of a plain halo, which demonstrates the amorphous nature of the product.

In another general aspect there is provided a process for the preparation of a salt of the amorphous form of esomeprazole. The process includes preparing a solution of a salt of esomeprazole in one or more solvents; and recovering the salt of esomeprazole in the amorphous form from the solution thereof by the removal of the solvent.

Embodiments of the process may include one or more of the following features. For example, the cation may be selected from the group that includes Na, Mg, Li, K, Ca, and N(R)$_4$, where R is hydrogen or an alkyl with 1-4 carbon atoms.

The solvent may be one or more of lower alkanol, ketone, ester, chlorinated solvent, acetonitrile or mixtures thereof. The lower alkanol may include one or more of primary, secondary and tertiary alcohol having from one to six carbon atoms. The lower alkanol may include one or more of methanol, ethanol, denatured spirit, n-propanol, isopropanol, n-butanol, isobutanol, and t-butanol. In particular, the lower alkanol may include one or more of methanol, ethanol, and denatured spirit.

The ketone may include one or more of acetone, 2-butanone, and 4-methylpentan-2-one. The ester may include one or more of ethyl acetate and n-butyl acetate. The chlorinated solvent may include one or more of chloroform and dichloromethane. Removing the solvent may include one or more of distillation, distillation under vacuum, evaporation, spray drying, and freeze drying.

The salt of esomeprazole in an amorphous form may be recovered from the solution by spray drying. Alternatively, the salt of esomeprazole in an amorphous form may be recovered from the solution by freeze-drying. The process may include further forming of the product so obtained into a finished dosage form.

The process may include further drying of the product obtained from the solution.

The process may further include adding one or both of an organic amine and ammonia to the solution. The organic amine and/or ammonia may be added to the solution prior to removal of the solvent. The process may produce the amorphous form of the salt of esomeprazole having the X-ray diffraction pattern of a plain halo, which demonstrates the amorphous nature of the product.

The details of one or more embodiments of the inventions are set forth in the description below. Other features, objects and advantages of the inventions will be apparent from the description and claims.

DETAILED DESCRIPTION OF THE INVENTION

The mentors have found a new form of esomeprazole salts, the amorphous form and, in particular, the amorphous esomeprazole magnesium salt. The new form is characterized by its X-ray powder diffraction pattern, which is described below as having a plain halo which demonstrates the amorphous nature of the product. The inventors also have developed a process for the preparation of the amorphous form of esomeprazole salts, including the esomeprazole magnesium salt, by recovering the amorphous esomeprazole salt from a solution thereof in a suitable solvent by spray drying. The resulting amorphous form of salts of esomeprazole include, for example, Na, Mg, Li, K, Ca, and $N(R)_4$, where R is hydrogen or an alkyl group with 1-4 carbon atoms. The inventors also have developed pharmaceutical compositions that contain the amorphous form of the esomeprazole salts, including the esomeprazole magnesium salt, in admixture with one or more solid or liquid pharmaceutical diluents, carriers, and/or excipients. These pharmaceutical compositions may be used for the treatment of gastric acid-related diseases by inhibition of gastric acid secretion.

In general, the solution of esomeprazole salt may be obtained by dissolving a crystalline esomeprazole salt in a suitable solvent. Alternatively, such a solution may be obtained directly from a reaction in which esomeprazole salt is formed. The solvent may be removed from the solution by a technique which includes, for example, distillation, distillation under vacuum, evaporation, spray drying, and freeze drying.

In one aspect, a salt of esomeprazole in amorphous form is recovered from the solution using a spray drying technique. A Mini-Spray Dryer (Model: Buchi 190, Switzerland) can be used. The Buchi 190 Mini-Spray Dryer operates on the principle of nozzle spraying in a parallel flow, i.e., the sprayed product and the drying gas flow in the same direction. The drying gas can be air or inert, gases such as nitrogen, argon and carbon dioxide.

In another aspect, a salt of esomeprazole in amorphous form can be recovered from the solution using a freeze drying technique. A freeze dryer (Model; Virtis Genesis SQ Freeze Dryer) can be used in this technique. The Virtis Genesis SQ Freeze Dryer operates on the principle of lyophilization, i.e., a process of stabilizing initially wet materials (aqueous solution or suspensions) by freezing them, then subliming the ice while simultaneously desorbing some of the bound moisture (primary drying). Following removal of the ice, desorption may be continued (secondary drying). This process may be carried out under vacuum.

The term "suitable solvent" includes any solvent or solvent mixture in which esomeprazole salt, including esomeprazole magnesium, is soluble, including, for example, nitriles, cyclic ethers, lower alkanol, ketones, esters, chlorinated solvents, acetonitrile and mixtures thereof. Examples of alcohols include methanol, ethanol, isopropanol, and the like. Examples of halogenated hydrocarbons include dichloromethane, dichloroethane, dibromoethane, and the like. Examples of nitrile include acetonitrile and the like. Examples of cyclic ethers include tetrahydroraran, dioxane, and the like. Examples of alkanol include those primary, secondary and tertiary alcohols having from one to six carbon atoms. Suitable lower alkanol solvents include methanol, ethanol, denatured spirit, n-propanol, isopropanol, n-butanol, isobutanol and t-butanol. Examples of ketones or esters include solvents such as acetone, 2-butanone, 4-methylpentan-2-one, ethyl acetate and n-butylacetate. A suitable chlorinated solvent includes one or both of dichloromethane and chloroform. Mixtures of all of these solvents are also contemplated.

An organic amine or ammonia may optionally be added to the solution of esomeprazole salt, including esomeprazole magnesium, before spray drying. The organic amine may be one or more of diethylamine, triethylamine, and the like. One purpose of adding the organic amine or ammonia is to provide stability to the esomprazole during processing.

If crystalline esomeprazole magnesium is used as a starting material it may be in the form of any of the various polymorphic forms known in the prior art including dihydrate form A, dihydrate form B, trihydrate, etc. Esomeprazole magnesium may he prepared by any of the known methods such as those cited in U.S. Pat. Nos. 5,714,504; 6,124,464; and 6,369,085. A solution of esomeprazole magnesium obtained in situ during the preparation process may be used as such for spray drying.

The spray drying may be accomplished using a spray dryer which operates on the principle of nozzle spraying in a parallel flow, i.e., the sprayed product and the drying gas flow in the same direction. The drying gas can be air or one or more inert gases such as nitrogen, argon, and carbon dioxide. Moreover, the product obtained may be further or additionally dried to achieve the desired moisture values. For example, the product may be further or additionally dried in a tray drier, dried under vacuum and/or in a Fluid Bed Dryer.

The resulting amorphous form of esomeprazole salt and, in particular, esomeprazole magnesium, may be formulated into ordinary dosage forms such as, for example, tablets, capsules, pills, solutions, etc. In these cases, the medicaments can be prepared by conventional methods with conventional pharmaceutical excipients. In. addition to the common dosage forms set out above, the amorphous form of esomeprazole magnesium may also be administered by controlled release means and/or delivery devices.

Further, the amorphous esomeprazole salt dosage forms described herein can be used in a method for treatment of gastric acid related diseases. The method of treatment includes administering to a mammal in need of treatment a dosage form that includes a therapeutically effective amount of the amorphous form of esomeprazole salt, including the esomeprazole magnesium salt.

The present inventions are further illustrated by the following examples which are provided merely to be exemplary of the inventions and are not intended to limit the scope of the invention. Although these examples are directed to amorphous esomeprazole magnesium, the principles described in these examples can be applied to other salts of amorphous esomeprazole.

Preparation of Amorphous form of Esomeprazole Magnesium

EXAMPLE 1

Esomeprazole magnesium trihydrate (200 g) was dissolved in a mixture of dichloromethane (1200 ml) and methanol (1200 ml) at 25-30° C., Any undissolved material was filtered off and triethylamine (2 ml) was added to the filtrate.

The clear solution thus obtained was spray dried in a mini spray dryer (Model Buchi—190) with an inlet temperature of 65-68° C. and an outlet temperature of 22-42° C. in 2 to 3 hours. The solid was further dried under vacuum at 60-65° C. for 14 to 15 hours to yield 120 g of esomeprazole magnesium of amorphous form. X-ray powder diffraction pattern showed a plain halo, which demonstrates the amorphous nature of the product. The following physical characteristics were obtained: Purity 99.77% by HPLC, Chiral purity 99.90% by HPLC, SOR 145.9°, Mg content 3.4.

EXAMPLE 2

Esomeprazole magnesium trihydrate (20 g) was dissolved in methanol (200 ml) at 25-30° C. Any undissolved material was filtered off and triethylamine (0.2 ml) was added to the filtrate. The clear solution thus obtained was subjected to spray drying with an inlet temperature of 65-68° C. and an outlet temperature of 22-42° C. The solid was further dried under vacuum at 60-65° C. for 14 to 15 hours to yield 11.5 g of esomeprazole magnesium of amorphous form.

EXAMPLE 3

Esomeprazole magnesium trihydrate (10 g) was dissolved in a mixture of dichloromethane (50 ml) and ethanol (70 ml) at 25-30° C. Any undissolved material was filtered off. The clear solution thus obtained was spray dried with an inlet temperature of 70-80° C. and an outlet temperature of 22-42° C. The solid was further dried under vacuum at 60-65° C. for 14 to 15 hours to yield 5.82 g of esomeprazole magnesium of amorphous form.

EXAMPLE 4

Esomeprazole magnesium trihydrate (100 g) was dissolved in methanol (1000 ml) at 25-30° C. Any undissolved material was filtered off. The clear solution thus obtained was spray dried with an inlet temperature of 65-68° C. and an outlet temperature of 22-42° C. The solid was further dried under vacuum at 60-65° C. for 14 to 15 hours to yield 55g of esomeprazole magnesium of amorphous form.

While several particular forms of the Inventions have been described, it will be apparent that various modifications and combinations of the inventions detailed in the text can be made without departing from the spirit and scope of the inventions. Further, it is contemplated that any single feature or any combination of optional features of the inventive variations described herein may be specifically excluded from the claimed inventions and be so described as a negative limitation. Accordingly, it is not intended that the inventions be limited, except as by the appended claims.

We claim:

1. A process for the preparation of a salt of the amorphous form of esomeprazole, the process comprising:
   preparing a solution of a salt of esomeprazole in at least one organic solvent, wherein the organic solvent contains an organic amine or ammonia, and
   recovering the salt of esomeprazole in the amorphous form from the solution thereof by the removal of the solvent.

2. The process of claim 1, wherein a cation is selected from the group consisting of Na, Mg, Li, K, Ca, and $N(R)_4$, where R is a hydrogen or an alkyl group with 1-4 carbon atoms.

3. The process of claim 2, wherein the cation is Na.

4. The process of claim 2, wherein the cation is Mg.

5. The process of claim 2, wherein the cation is K.

6. The process of claim 2, wherein the cation is Ca.

7. The process of claim 1, wherein the solvent is at least one of a lower alkanol, ketone, ester, chlorinated solvent, acetonitrile or mixtures thereof.

8. The process of claim 7, wherein the lower alkanol is selected from a primary, secondary or tertiary alcohol having from one to six carbon atoms.

9. The process of claim 7, wherein the lower alkanol is methanol, ethanol, denatured spirit, n-propanol, isopropanol, n-butanol, isobutanol, and t-butanol or a mixture thereof.

10. The process of claim 7, wherein the ketone is selected from acetone, 2-butanone, and 4-methylpentan-2-one or a mixture thereof.

11. The process of claim 7, wherein the ester is selected from ethyl acetate, n-butyl acetate or a mixture thereof.

12. The process of claim 7, wherein the chlorinated solvent is selected from chloroform, dichloromethane or a mixture thereof.

13. The process of claim 1, wherein removing the solvent comprises one or more of distillation, distillation under vacuum, evaporation, spray drying, and freeze drying.

14. The process of claim 1, wherein the salt of esomeprazole in an amorphous form is recovered from the solution by spray drying.

15. The process of claim 1, wherein the salt of esomeprazole in an amorphous form is recovered from the solution by freeze-drying.

16. The process of claim 1, further comprising additional drying of the product obtained.

* * * * *